United States Patent [19]

Grutke et al.

[11] Patent Number: 6,011,099
[45] Date of Patent: Jan. 4, 2000

[54] OXIDATION-STABILIZED POLYAMIDE MOLDING MATERIALS

[75] Inventors: Stefan Grutke, Neustadt; Peter Comba, Neckargemünd; Charis Katsichtis, Heidelberg, all of Germany

[73] Assignee: BASF Aktiengesellschaft, Ludwigshafen, Germany

[21] Appl. No.: 09/171,198

[22] PCT Filed: Apr. 17, 1997

[86] PCT No.: PCT/EP97/01910

§ 371 Date: Oct. 15, 1998

§ 102(e) Date: Oct. 15, 1998

[87] PCT Pub. No.: WO97/40100

PCT Pub. Date: Oct. 30, 1997

[30] Foreign Application Priority Data

Apr. 19, 1996 [DE] Germany ............... 196 15 484

[51] Int. Cl.⁷ ...................................... C08K 3/32
[52] U.S. Cl. ................. 524/414; 524/154; 524/413
[58] Field of Search ................... 524/413, 414, 524/154

[56] References Cited

U.S. PATENT DOCUMENTS 3,294,870 12/1966 Grayson et al. ............ 524/154
3,505,285 4/1970 Hermann et al. ............ 524/154
5,550,305 8/1996 Wu ............................ 585/513
5,710,216 1/1998 Weber et al. ................ 525/132

FOREIGN PATENT DOCUMENTS 463 512  1/1992  European Pat. Off. .

OTHER PUBLICATIONS

Chompness et al., J.Chem.Soc.,Dalton Trans., 20, 3031–7, 1994.

Kyba et al. J.Am.Chem.Soc., 107, 2141–8, 1985.

Chem. Abst., vol. 122, No. 4, AN 44921.

Chem. Abst., vol. 102, No. 17, 149381.

Chem. Abst., vol. 98, No. 6, 45858.

Chem. Abst., vol. 97, No. 9, 71596.

*Primary Examiner*—David W. Wu
*Assistant Examiner*—Ling Sui Choi
*Attorney, Agent, or Firm*—Keil & Weinkauf

[57] ABSTRACT

A thermoplastic molding material comprising a mixture of a polyamide and a stabilizing amount of a copper compound obtained by reacting a copper(I) salt with a phosphine chelate ligand containing at least 2 phosphorous atoms.

8 Claims, No Drawings

OXIDATION-STABILIZED POLYAMIDE MOLDING MATERIALS

The present invention relates to thermoplastic molding materials containing
- from 30 to 100% by weight of a mixture of polyamide and a stabilizing amount of a copper compound obtainable by reacting copper(I) salts with phosphine chelate ligands and
- from 0 to 70% by weight of further additives.

The present invention furthermore describes novel phosphorus-sulfur compounds and the use of phosphine chelate ligands in copper compounds for stabilizing thermoplastic molding materials. The present invention furthermore relates to the use of the molding materials for the production of moldings of any type and to the moldings obtainable thereby.

The poor stability of polyamides to thermal oxidation has long been known, but the oxidative degradation of the polyamide surface is not sufficiently inhibited with the stabilizers known to date.

For example, EP-A 463 512 describes stabilizer combinations comprising copper(I) halides, triphenylphosphine and amines for toughened polyamides. The addition of amine antioxidants often causes direct discolorations and discolorations on exposure to heat.

CH-A 472 458 discloses the addition of copper(I) salts and triphenylphosphine, particularly in combination with potassium iodide, as a heat stabilizer to the polyamides. These polyamides nevertheless have unsatisfactory heat stability, which is reflected in the deterioration in the impact strength and in the modulus of elasticity. Apart from this, owing to their solubility in water, the stabilizers frequently form a deposit and hence defects which lead to spots and discolorations.

It is an object of the present invention to provide thermoplastic molding materials which exhibit improved heat stabilization and in addition show less tendency to discoloration.

We have found that this object is achieved by the thermoplastic molding materials defined above.

The copper compounds added for stabilization are obtainable by reacting copper(I) salts with known and novel phosphine chelate ligands. The present invention furthermore relates to phosphorus-sulfur compounds of the formula II which may be used as chelate ligands.

Suitable copper(I) salts are both copper salts of organic acids, for example acetic acid, and those of inorganic acids, such as hydrocyanic acid or thiocyanic acid, preferably those of hydrohalic acids. From the group consisting of the copper halides, ie. copper fluoride, copper chloride, copper bromide and copper iodide, the three last-mentioned are preferred, copper iodide being particularly suitable.

Compounds of the general formula (I)

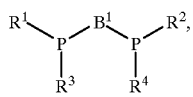

(I)

where
- $B^1$ is $C_1$–$C_6$-alkylene, naphthylene, phenylene or benzylene,
- $R^1$ und $R^2$, independently of one another, are each $C_1$–$C_8$-alkyl, $C_5$–$C_8$-cycloalkyl or phenyl which is unsubstituted or monosubstituted to penta substituted by $C_1$–$C_4$-alkyl,
- $R^3$ und $R^4$, independently of one another, are each $C_1$–$C_8$-alkyl, $C_5$–$C_8$-cycloalkyl, phenyl which is unsubstituted or substituted by $C_1$–$C_4$-alkyl, or are each —$B^1$—$PR^2R^2$, $B^2$—$SR^5$ or $B^2$—$OR^5$, and $R^3$ und $R^4$ together are —$B^2$—$PR^2$—$B^3$— or —$B^2$—$PR^2$—$B^3$—$PR^2$—$B^4$—, and $B^2$, $B^3$ and $B^4$, independently of one another, are each $C_1$–$C_6$-alkylene, naphthylene, phenylene or benzylene and
- $R^5$ is $C_1$–$C_4$-alkyl or hydrogen, may advantageously be used as phosphine chelate ligands.

Suitable substituents $B^1$, $B^2$, $B^3$ and $B^4$, independently of one another, are methylene, ethylene, n-propylene, isopropylene, n-butylene, n-pentylene, n-hexylene, 1,1'- or 2,2'-naphthylene, 1,4-phenylene and para-benzylene.

Suitable substituents $R^1$, $R^2$, $R^3$, $R^4$ and $R^5$, independently of one another, are methyl, ethyl, n-propyl, isopropyl, n-butyl, isobutyl, sec-butyl and tert-butyl.

$R^1$, $R^2$, $R^3$ and $R^4$ are furthermore, for example, pentyl, isopentyl, neopentyl, tert-pentyl, hexyl, 2-methylpentyl, heptyl, octyl, 2-ethylhexyl, isooctyl, cyclopentyl, cyclohexyl, cycloheptyl, cyclooctyl, 2-, 3- or 4-methylphenyl, 2-, 3- or 4-ethylphenyl, 4-isopropylphenyl, 2,4,6-trimethylphenyl, 2,4-dimethylphenyl or 4-tert-butylphenyl.

Preferred copper compounds are those which are obtained by reaction with phosphine chelate ligands of the general formula (II)

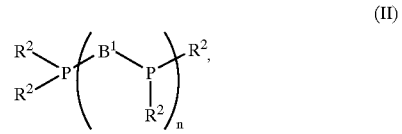

(II)

where $B^1$ and $R^2$ have the above meanings and n is 1, 2 or 3.

Phosphine chelate ligands in which $B^1$ is a methylene, ethylene, propylene, butylene or naphthylene bridge are also preferred.

$R^1$, $R^2$, $R^3$ and/or $R^4$ are preferably straight-chain alkyls. Unsubstituted phenyl is furthermore preferred.

Phosphine chelate ligands in which $R^1$ and $R^2$ are each cyclohexyl or phenyl are particularly preferred.

Phosphine chelate ligands II in which n is 1 are also particularly preferred.

Examples of suitable phosphine chelate ligands are 1,2-bis-(dimethylphosphino)ethane, bis-(2-diphenylphosphinoethyl)phenylphosphine, 1,6-bis(diphenylphosphino)hexane and 1,5-bis(diphenylphosphino)pentane.

Examples of particularly preferred phosphine chelate ligands are bis-(diphenylphosphino)methane, 1,2-bis(diphenylphosphino)ethane, 1,3-bis(diphenylphosphino)propane, 2,2'-bis(diphenylphosphino)1,1'-binaphthyl, 1,3-bis(dicyclohexylphosphino)propane and 1,4-bis(diphenylphosphino)butane.

The phosphine chelate ligands can be prepared by the reactions generally known for organophosphorus compounds, as described in Advanced Organic Chemistry: Reactions, Mechanisms and Structure, J. March, Wiley-Interscience Publication, 4 (1992), 413, and Inorg. Chemistry of the Transition Elements, Vol. 6, The Chemical Society, 1978, Johnson, Gilbert, page 272 et seq., Methoden der organischen Chemie, Houben-Weyl, XII/1, Georg Thieme Verlag, Stuttgart, 1963, pages 17–66, for example by reacting phosphorus halides with Grignard compounds or by reacting phosphines with alkyl halides under reducing conditions, for example using sodium amide in liquid ammonia or sodium in liquid ammonia. Using the same reaction principle, it is possible to link two phosphines by an alkylene or arylene bridge by choosing dihaloalkanes or dihaloaromatics or monoalkylphosphines or arylphosphines.

Some of the phosphine chelate ligands are commercially available.

The present application furthermore relates to novel phosphorus-sulfur compounds of the general formula (III)

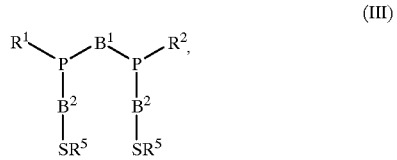

(III)

where $B^1$ and $B^2$, independently of one another, are each $C_1$–$C_6$-alkylene, naphthylene, phenylene or benzylene, $R^1$ and $R^2$, independently of one another, are each $C_1$–$C_8$-alkyl, $C_5$–$C_8$-cycloalkyl or phenyl which is unsubstituted or substituted by $C_1$–$C_4$-alkyl and $R^5$ is $C_1$–$C_4$-alkyl or hydrogen.

The preparation of the novel phosphine chelate ligands III is likewise carried out by known reactions.

In a first reaction step, for example 2 mol of a monoalkylphosphine are reacted with one mole of a dibromoalkane under reducing conditions, for example using sodium in liquid ammonia, to give the bisphosphine IV, according to the following general equation

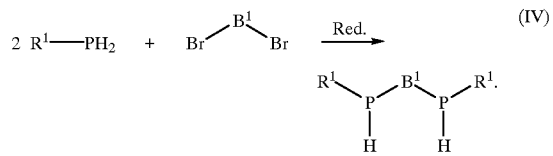

(IV)

The further synthesis is carried out by reacting IV with a monothiacycle, once again under reducing conditions, with ring cleavage. The dithiol thus obtained can, if required, be converted into its thioether by known reactions.

The term chelate ligands is intended merely to express the fact that the phosphine compounds have a plurality of coordination sites for possible complexing.

The phosphine chelate ligands are reacted with the copper (I) salt in a molar ratio of from 1:1 to 5:1. From one to three times the molar amount of phosphine chelate ligand is preferably chosen. It is assumed that the copper(I) salts form coordinate bonds with the phosphine chelate ligands so that mixtures of differently coordinated copper compounds can of course also occur in the presence of a plurality of coordination sites. Depending on the chosen ratio of phosphine chelate ligand to copper(I) salt, unreacted ligand may also be present in the mixture, although this is not disadvantageous.

For the preparation of the copper compound, the copper(I) halides are reacted with the phosphine chelate ligands in an inert solvent/diluent or in the melt in the absence of a solvent.

Examples of the inert solvents/diluents are ketones, such as acetone and cyclohexane, cyclic ethers, such as tetrahydrofuran and dioxane, dialkyl ethers, such as diethyl ether, and halohydrocarbons, such as methylene chloride, dichloroethane, carbon tetrachloride and chloroform. Acetone, tetrahydrofuran and chloroform are preferred as solvents.

The reaction in the melt is preferred since the solvent does not have to be subsequently removed.

In a preferred embodiment, the copper(I) salt is metered into the molten or dissolved phosphine chelate ligand.

It is also advantageous to add a solution of the phosphine chelate ligand to the copper(I) salt. It is possible to carry out the reaction at as low as room temperature. A temperature range of from 20 to 60° C. is particularly advisable. Depending on the chosen temperature, the reaction is complete after from 2 to 8 hours, longer reaction times being required at the lower temperatures and vice versa.

Temperatures above the respective melting point, as a rule from 130 to 350° C., preferably from 240 to 280° C., are required for the reaction in the melt.

Since the unreacted copper(I) salt is present in suspension, it is advantageous to carry out stirring during the reaction.

The reaction in an inert gas atmosphere, such as nitrogen, is advantageous, although not essential, since the stability of the copper compounds to oxidation declines slightly at higher temperatures, such as in the melt.

It has now been found that the copper compounds obtained by reacting copper(I) salts with phosphine chelate ligands are very useful for stabilizing thermoplastic molding materials containing from 30 to 100% by weight of polyamide and from 0 to 70% by weight of further additives.

The molding materials preferbaly contain the copper compound in an amount of from 10 to 1000 ppm, particularly preferably from 50 to 500 ppm, calculated as copper and based on polyamide. Larger amounts of copper compound, for example 2, preferably 1, % by weight in masterbatches, are possible.

The novel molding materials contain from 30 to 100, preferably from 40 to 90, in particular from 60 to 80, % by weight of a mixture of polyamide and a stabilizing amount of a copper compound obtainable by reacting copper(I) salts with phosphine chelate ligands (Component A).

The polyamides of the novel molding materials have in general a relative viscosity Ire, of from 1.7 to 5.0, determined in a 1% strength by weight solution in 96% strength by weight sulfuric acid at 25° C. Polyamides having a relative viscosity of from 1.7 to 4.5, in particular from 2.5 to 4.0, are preferably used.

These relative viscosities of from 2.5 to 4.0 correspond to the viscosity numbers (VN) from 120 to 220 ml/g (measured according to ISO 307, DIN 53727).

Semicrystalline or amorphous resins having a weight average molecular weight of at least 5000, as described, for example, in U.S. Pat. Nos. 2,071,250, 2,071,251, 2,130,523, 2,130,948, 2,241,322, 2,312,966, 2,512,606 and 3,393,210, are preferred.

Examples of these are polyamides derived from lactams having from 7 to 13 ring members, such as polycaprolactam, polycapryllactam and polylaurolactam, and polyamides which are obtained by reacting dicarboxylic acids with diamines.

Dicarboxylic acids which can be used are alkanedicarboxylic acids of 6 to 12, in particular 6 to 10, carbon atoms and aromatic dicarboxylic acids. Examples of these acids are adipic acid, azelaic acid, sebacic acid, dodecandioc acid and terephthalic and/or isophthalic acid.

Particularly suitable diamines are alkanediamines of 6 to 12, in particular 6 to 8, carbon atoms and m-xylylenediamine di-(4-aminophenyl)methane, di-(4- aminocyclohexyl)methane, 2,2-di(4-aminophenyl)propane and 2,2-di-(4-aminocyclohexyl)propane.

Preferred polyamides are polyhexamethyleneadipamide, polyhexamethylenesebacamide and polycaprolactam.

Polyamides which are obtainable, for example, by condensation of 1,4-diaminobutane with adipic acid at elevated temperatures (polyamide 4,6) may also be mentioned. Preparation processes for polyamides having this structure are described, for example, in EP-A 38 094, EP-A 38 582 and EP-A 39 524.

Polyamides which are obtainable by copolymerization of two or more of the abovementioned monomers, or mixtures of a plurality of polyamides, any desired mixing ratio being possible, are also suitable.

Such partly aromatic, semicrystalline copolyamides are composed, for example, of:

$A_1$) 20–90% by weight of units derived from terephthalic acid and hexamethylenediamine, $A_2$) 0–50% by weight of units derived from ε-caprolactam and $A_3$) 0–80% by weight of units derived from adipic acid and hexamethylenediamine, $A_4$) 0–40% by weight of further polyimide-forming monomers, the amount of component ($A_2$) and/or ($A_3$) and/or ($A_4$) being at least 10% by weight.

The component $A_1$) contains 20–90% by weight of units derived from terephthalic acid and hexamethylenediamine.

In addition to the units derived from terephthalic acid and hexamethylenediamine, the copolyamides contain units derived from ε-caprolactam and/or units derived from adipic acid and hexamethylene diamine and/or units derived from further polyamide-forming monomers.

The amount of units derived from ε-caprolactam is not more than 50, preferbaly from 20 to 50, in particular from 25 to 40, % by weight, while the amount of units derived from adipic acid and hexamethylenediamine is up to 80, preferably from 30 to 75, in particular from 35 to 60, % by weight.

The copolyamides may also contain both the units of ε-caprolactam and units of adipic acid and hexamethylenediamine; in this case, it is advantageous if the amount of units which are free of aromatic groups is at least 10, preferably at least 20, % by weight. The ratio of units derived from ε-caprolactam to those derived from adipic acid and hexamethylenediamine is not subject to any particular restriction.

Polyamides containing from 50 to 80, in particular from 60 to 75, % by weight of units derived from terepthalic acid and hexamethylenediamine (units $A_1$)) and from 20 to 50, preferably from 25 to 40, % by weight of units derived from ε-caprolactam (units $A_2$)) have proven particularly advantageous for many intended uses.

In addition to the units $A_1$) to $A_3$) described above, the partly aromatic copolyamides may contain up to 40, preferably 10–30, in particular 20–30, % by weight of further polyamide-forming monomers $A_4$), such as those known from other polyamides.

Aromatic dicarboxylic acids $A_4$) are of 8 to 16 carbon atoms. Examples of suitable aromatic dicarboxylic acids are isophthalic acid, substituted terephthalic and isophthalic acids, such as 3-tert-butylisophthalic acid, polynuclear dicarboxylic acids, e.g. 4,4'- and 3,3'-diphenyldicarboxylic acid, 4,4'- and 3,3'-diphenylmethanedicarboxylic acid, 4,4'- and 3,3'-dicarboxydiphenyl sulfone, 1,4- and 2,6-naphthalinedicarboxylic acid and phenoxyterephthalic acid, isophthalic acid being articularly preferred.

Further polyamide-forming monomers $A_4$) may be derived from dicarboxylic acids of 4 to 16 carbon atoms and aliphatic or cycloaliphatic diamines of 4 to 16 carbon atoms and from aminocarboxylic acids or corresponding lactams of 7 to 12 carbon atoms. Examples of suitable monomers of these types include suberic acid, azelaic acid and sebacic acid as typical aliphatic dicarboxylic acids, 1,4-butanediamine, 1,5-pentanediamine and piperazine as typical diamines and capryllactam, enantholactam, (ω-aminoundecanoic acid and laurolactam as typical lactams and aminocarboxylic acids.

Here, the following compositions of component (A) are particularly preferred:

$A_1$) from 65 to 85% by weight of units derived from terephthalic acid and hexamethylenediamine and $A_4$) from 15 to 35% by weight of units derived from isophthalic acid and hexamethylenediamine or $A_1$) from 50 to 70% by weight of units derived from terephthalic acid and hexamethylenediamine and $A_3$) from 10 to 20% by weight of units derived from adipic acid and hexamethylenediamine and $A_4$) from 20 to 30% by weight of units derived from isophthalic acid and hexamethylenediamine.

If component ($A_4$) contains symmetrical dicarboxylic acids in which the carboxyl groups are in the para position, it is advisable to combine this with ($A_1$) and ($A_2$) or ($A_1$) and ($A_3$) to give ternary copolyamides, since otherwise the copolyamide has too high a melting point and melts only with decomposition, which is undesirable.

If component ($A_4$) contains cylic aliphatic diamines as polyamide building blocks, particularly preferred diamine components here are bis(4-amineocyclohexyl)methane, bis(4-amino-3-methylcyclohexyl)methane, 2,2-bis(4-aminocyclohexyl)propane, 2,2-bis(4-amino-3-methylcyclohexyl)propane, cyclohexanediamine and isophoronediamine. Such partly aromatic, semicrystalline polyamides are described in DE-A 44 04 250.

Partly aromatic copolyamides whose triamine content is less than 0.5, preferably less than 0.3, % by weight have also proven particularly advantageous. These copolyamides can be prepared by the processes described in EP-A 129 195 and 129 196.

The novel thermoplastic molding materials may contain, as further component, from 0 to 70, preferably up to 35, in particular from 15 to 35, % by weight of further additives. These are in particular fibrous or particulate fillers (component B) or elastomeric polymers (component C) and mixtures thereof.

Preferred fibrous reinforcing materials are carbon fibers, potassium titanate whiskers, aramid fibers and particularly preferably glass fibers. when glass fibers are used, they may be provided with a size and an adhesion promoter to ensure better compatibility with the thermoplastic polyamide. In general, the glass fibers used have a diameter of from 6 to 20 μm, preferably from 10 to 14 μm.

These glass fibers may be incorporated in the form of both short glass fibers and rovings. In the finished injection molded part, the average length of the glass fibers is preferably from 0.08 to 0.5 mm.

Suitable particulate fillers are amorphous silica, magnesium carbonate (chalk), kaolin (in particular calcined kaolin), powdered quartz, mica, talc, feldspar and in particular calcium silicates, such as wollastonite.

Preferred combinations of fillers are, for example, 20% by weight of glass fibers with 15% by weight of wollastonite and 15% by weight of glass fibers with 15% by weight of wollastonite.

The molding materials may contain from 0 to 30, preferably up to 20, in particular from 10 to 15, % by weight of an elastomeric polymer C (often also referred to as an impact modifier or rubber). Preferred elastomeric polymers are polymers based on olefins which are composed of the following components:

$C_1$) from 40 to 100% by weight of at least one α-olefin of 2 to 8 carbon atoms, $C_2$) from 0 to 50% by weight of a diene, $C_3$) from 0 to 45% by weight of a $C_1$–$C_{12}$-alkyl ester of acrylic acid or methacrylic acid or mixtures of such esters, $C_4$) from 0 to 40% by weight of an ethylenically unsaturated mono- or dicarboxylic acid or a functional derivative of such an acid, $C_5$) from 0 to 40% by weight of an epoxy-containing monomer and $C_6$) from 0 to 5% by weight of other monomers capable of free radical polymerization, with the proviso that component (C) is not an olefin homopolymer.

A first preferred group comprises the ethylene/propylene (EPM) and ethylene/propylene/diene (EPDM) rubbers, which preferably have a ratio of ethylene to propylene units of from 40:60 to 90:10.

The Mooney viscosities (MLI+4/100° C.) of such, preferably uncrosslinked, EPM and EPDM rubbers (gel contents in general less than 1% by weight) are preferably from 25 to 100, in particular from 35 to 90 (measured using the large rotor after a running time of 4 minutes at 100° C. according to DIN 53 523).

EPM rubbers generally have virtually no more double bonds, whereas EPDM rubbers may have from 1 to 20 double bonds/100 carbon atoms.

Examples of diene monomers $C_2$) for EPDM rubbers are conjugated dienes, such as isoprene and butadiene, nonconjugated dienes of 5 to 25 carbon atoms, such as penta-1,4-diene, hexa-1,4-diene, hexa-1,5-diene, 2,5-dimethylhexa-1,5-diene and octa-1,4-diene, cyclic dienes, such as cyclopentadiene, cyclohexadienes, cyclooctadienes and dicyclopentadiene, and alkenylnorbornenes, such as 5-ethylidene-2-norbornene, 5-butylidene-2-norbornene, 2-methallyl-5-norbornene and 2-isopropenyl-5-norbornene, and tricyclodienes, such as 3-methyltricyclo[5.2.1.0.2.6]-3,8-decadiene, and mixtures thereof. Hexa-1,5-diene, 5-ethylidenenorbornene and dicyclopentadiene are preferred. The diene content of the EPDM rubbers is preferably from 0.5 to 50, in particular from 2 to 20, particularly preferably from 3 to 15, % by weight, based on the total weight of the olefin polymer.

EPM and EPDM rubbers may preferbaly also be grafted with reactive carboxylic acids or derivatives thereof. Particular examples of these are acrylic acid, methacrylic acid and derivatives thereof and maleic anhydride.

A further group of preferred olefin polymers comprises copolymers of α-olefins of 2 to 8 carbon atoms, in particular of ethylene, with $C_1$–$C_{18}$-alkyl esters of acrylic acid and/or methacrylic acid.

All primary and secondary $C_1$–$C_{18}$-alkyl esters of acrylic acid or methacrylic acid are in principle suitable, but esters of 1 to 12, in particular 2 to 10, carbon atoms are preferred.

Examples of these are methyl, ethyl, propyl, n-butyl, isobutyl, 2-ethylhexyl, octyl and decyl acrylates and the corresponding esters of methacrylic acid. Among these, n-butyl acrylate and 2-ethylhexyl acrylate are particularly preferred.

The amount of methacrylates and acrylates $C_3$) in the olefin polymers is 0–60, preferably 10–50, in particular 30–45, % by weight.

Instead of the esters $C_3$) or in addition to them, the olefin polymers may also contain, as monomers, ethylenically unsaturated mono- or dicarboxylic acids $C_4$) having acid functional groups and/or latent acid functional groups or epoxy-containing monomers $C_5$).

Examples of monomers $C_4$) are acrylic acid, methacrylic acid, tertiary alkyl esters of these acids, in particular tert-butyl acrylate, and dicarboxylic acids, such as maleic acid and fumaric acid and derivatives of these acids and monoesters thereof.

Monomers having latent acid functional groups are to be understood as meaning those compounds which form free acid groups under the polymerization conditions or during incorporation of the olefin polymers into the molding materials. Examples of these are anhydrides of dicarboxylic acids of up to 20 carbon atoms, in particular maleic anhydride, and tertiary $C_1$–$C_{12}$-alkyl esters of the abovementioned acids, in particular tert-butyl acrylate and tert-butyl methacrylate.

The monomers having acid functional groups or latent acid functional groups and the epoxy-containing monomers are preferably incorporated into the olefin polymers by adding to the monomer mixture compounds of the general formulae IV–VII

(IV)

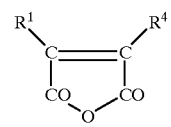

(V)

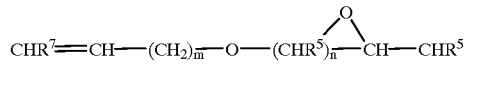

(VI)

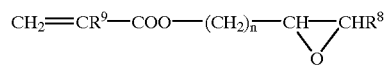

(VII)

where $R^1$ to $R^9$ are each hydrogen or alkyl of 1 to 6 carbon atoms, m is an integer from 0 to 20 and n is an integer from 0 to 10.

$R^1$ to $R^7$ are each preferably hydrogen, m is preferably 0 or 1 and n is preferably 1. The corresponding compounds are maleic acid, fumaric acid and maleic anhydride $C_4$) or alkenyl glycidyl ether and vinyl glycidyl ether $C_5$).

Preferred compounds of the formulae IV, V, VI and VII are maleic acid and maleic anhydride as component $C_4$) and epoxy-containing esters of acrylic acid and/or methacrylic acid, particularly preferably glycidyl acrylate and glycidyl methacrylat, (as component $C_5$).

The amount of components $C_4$) and $C_5$) is in each case from 0.07 to 40, in particular from 0.1 to 20, particularly preferably from 0.15 to 15, % by weight, based on the total weight of the olefin polymers.

Olefin polymers of from 50 to 98.9, in particular from 60 to 95, % by weight of ethylene, from 0.1 to 20, in particular from 0.15 to 15, % by weight of glycidyl acrylate and/or glycidyl methacrylate, acrylic acid and/or maleic anhydride, and from 1 to 45, in particular from 10 to 35, % by weight of n-butyl acrylate and/or 2-ethylhexyl acrylate are particularly preferred.

Further preferred esters of acrylic and/or methacrylic acid are the methyl, ethyl, propyl and isobutyl esters.

For example, vinyl esters and vinyl ethers are suitable as other monomers $C_6$).

The ethylene copolymers described above can be prepared by processes known per se, preferably by random copolymerization under high pressure and at elevated temperatures.

The melt flow index of the ethylene copolymers is in general from 1 to 80 g/10 min (measured at 190° C. and 2.16 kg load).

In addition to the above preferred elastomeric polymers based on olefins, suitable elastomers (C) are, for example, emulsion polymers, the preparation of which is described, for example, in Houben-Weyl, Methoden der organischen Chemie, Vol. XII. I (1961), and by Blackley in the monograph "Emulsion Polymerisation".

In principle, random elastomers or those having a shell morphology may be used. The shell-like morphology is determined by the order of addition of the individual monomers.

Examples of monomers for the preparation of the elastomers are acrylates, such as n-butyl acrylate and 2-ethylhexyl acrylate, corresponding methacrylates and mixtures thereof. These monomers may be copolymerized with further monomers, such as styrene, acrylonitrile, vinyl ethers and further acrylates or methacrylates, such as methyl methacrylate, methyl acrylate, ethyl acrylate and propyl acrylate.

It is advantageous to use emulsion polymers which have reactive groups at the surface. Such groups are, for example, epoxy, carboxyl, latent carboxyl, amino and amido groups.

The graft monomers described in EP-A 208 187 are also suitable for introducing reactive groups at the surface.

Furthermore, the emulsion polymers may be completely or partially crosslinked. Monomers which act as crosslinking agents are, for example, buta-1,3-diene, divinylbenzene, diallyl phthalate and dihydrodicyclopentadienyl acrylate and the compounds described in EP-A 50 265.

Graft-linking monomers, ie. monomers having two or more polymerizable double bonds which react at different rates in the polymerization, may also be used.

Examples of such graft-linking monomers are allyl-containing monomers, in particular allyl esters of ethylenically unsaturated carboxylic acids, such as allyl acrylate, allyl methacrylate, diallyl maleate, diallyl fumarate, diallyl itaconate and the corresponding monoallyl compounds of these dicarboxylic acids. There are also a large number of further suitable graft-linking monomers; for further details, reference may be made to, for example, U.S. Pat. No. 4,148,846.

In general, the amount of these crosslinking monomers in component (C) is up to 5, preferably not more than 3, % by weight based on (C).

Examples of preferred emulsion polymers are n-butyl acrylate/(meth)acrylic acid copolymers, n-butyl acrylate/ glycidyl acrylate or n-butyl acrylate/glycidyl methacrylate copolymers and graft polymers having an inner core of n-butyl acrylate and an outer shell of the abovementioned copolymers.

The elastomers (C) described can also be prepared by other conventional processes, for example by suspension polymerization.

Further conventional additives are, for example, stabilizers and antioxidants, heat stabilizers and UV stabilizers, lubricants and mold release agents, dyes and pigments, plasticizers and processing assistants. Their amopreferably up to 30, preferably up to 15, % by weight based on the total weight of the molding materials.

Pigments and dyes are generally present in amounts of up to 4, preferably from 0.5 to 3.5, in particular from 0.5 to 3, % by weight.

The pigments for coloring thermoplastics are generally known (cf. for example R. Gächter and H. Müller, Taschenbuch der Kunststoffadditive, Carl Hanser Verlag, 1983, pages 494 to 510). A first preferred group of pigments comprises white pigments, such as zinc oxide, zinc sulfide, lead white (2 $PbCO_3.Pb(OH)_2$), lithopone, antimony white and titanium dioxide. Of the two most commonly used crystal modifications (rutile and anatase) of titanium dioxide, the rutile form in particular is used for imparting whiteness to the novel molding materials.

Black pigments which may be used according to the invention are iron oxide black ($Fe_3O_4$), spinel black (Cu(Cr, Fe)$_2O_4$), manganese black (mixture of manganese dioxide, silica and iron oxide), cobalt black and antimony black and particularly preferably carbon black, which is generally used in the form of furnace black or gas black (in this context, cf. G. Benzing, Pigmente für Anstrichmittel, Expert-Verlag (1988), page 78 et seq.).

Of course, inorganic colored pigments, such as chromium oxide green, or organic color pigments, such as azo pigments and phthalocyanines, may be used according to the invention for obtaining certain hues. Such pigments are in general commercially available.

It may furthermore be advantageous to use the stated pigments or dyes as a mixture, for example carbon black with copper phthalocyanines, since the color dispersion of the thermoplastic is generally facilitated.

Examples of UV stabilizers are various substituted resorcinols, salicylates, benzotriazoles and benzophenones, which are generally used in amounts of up to 2% by weight.

Lubricants and mold-release agents, which are added to the thermoplastic material as a rule in amounts of up to 1% by weight, are stearic acid, stearyl alcohol, alkyl stearates and stearamides and esters of pentaerythritol with long-chain fatty acids. Salts of calcium, of zinc or of aluminum with stearic acid and dialkyl ketones, e.g. distearyl ketone, may also be used.

The additives include stabilizers which prevent the decomposition of red phosphorus in the presence of moisture and atmospheric oxygen. Examples are compounds of cadmium, of zinc, of aluminum, of tin, of magnesium, of manganese and of titanium. Particularly suitable compounds are, for example, oxides of the stated metals and carbonates or basic carbonates, hydroxides and salts of organic or inorganic acids, such as acetates or phosphates or hydrogen phosphates.

The only flameproofing agents mentioned here are red phosphorus and the other flameproofing agents known per se for polyamides.

The novel thermoplastic molding materials can be prepared by methods known per se, by mixing the starting components in conventional mixing apparatus, such as an extruder, a Brabender mill or a Banbury mill, and then extruding the mixture. After extrusion, the extrudate is cooled and comminuted.

The stabilizing copper compound may be added directly to the liquid polyamide via a side extruder or may be metered into the polyamide as a masterbatch.

The addition in an early processing step is preferred since any oxidative damage due to the processing can thus be avoided.

In a particular preferred embodiment, it is also possible, if desired, to meter the components B) and/or C) into the prepolymer of component A) in the devolatilation extruder, in which case the devolatilation extruder is usually equipped with suitable mixing elements, such as kneading blocks. The mixture is then likewise extruded, cooled and granulated.

The novel molding materials have relatively high heat distortion resistance. In particular, they can be readily processed by a thermoplastic method and accordingly are suitable for the production of fibers, films and moldings. They also give substantially better results when colored.

A further increase in the heat stabilization can be achieved by adding alkali metal halides. From the group consisting of the lithium, sodium and potassium halides, the potassium salts are preferred. Examples of suitable halides are the fluorides, chlorides and, preferably, the bromides and iodides. The increase in the stabilization effect due to potassium bromide and potassium iodide is particularly noteworthy.

As a rule, the inorganic alkali metal halides are added to the molding material in an amount of from 1 to 3000 ppm, preferably from 10 to 1000 ppm, based on polyamide. They are usually added as mixtures with the copper compound.

The examples which follow illustrate the invention.

EXAMPLES

A. PREPARATION OF COPPER COMPOUNDS a) In the Prescence of a Diluent 10 g (0.062 mol) of copper(I) iodide in 40 ml of chloroform were initially taken under nitrogen, and 100 ml of a 1.25 molar solution (0.125 mol) of the phosphine chelate ligand were added dropwise to the suspension while stirring. The solvent was removed after the formation of a clear solution after from 2 to 8 hours.

b) Without Diluent 2 mol of phosphine chelate ligand were melted at from 140 to 142° C. under nitrogen, and 166 g (1 mol) of copper(I) iodide were added a little at a time over a period of 2 hours. After 3 hours, the reaction was complete.

B. General Preparation of the Thermoplastic Molding Materials (Beispiele 1 to 9)

Polyamide 66 having a viscosity number VN (0.5% strength by weight PA66 in 96% strength by weight sulfuric acid at 25° C.) of 150 ml/g (Ultramid® A3 from BASF AG) or polyamide 6 having a viscosity number VN (0.5% strength by weight P6 in 96% strength by weight sulfuric acid at 25° C.) of 150 ml/g (Ultramid® B3 from BASF AG) and, if required, glass fibers having a diameter of 10 μm (No. 3540 from PPG) and the corresponding copper compound and, if required, potassium iodide were compounded in a twin-screw extruder (ZSK 57 from Werner and Pfleiderer) in the ratios stated in Table 1. The concentration of the stabilizer systems was 250 ppm of copper and, if required, 750 ppm of potassium iodide, based on PA. The resulting granules were dried and were processed to give test specimens according to DIN 53455/53453.

In the same manner, polyamides were compounded with copper(I) iodide/triphenylphosphine (250 ppm of copper, based on polyamide) as stabilizer, if required with the glass fibers and, if required, potassium iodide (750 ppm of potassium iodide, based on polyamide), for comparison (Examples 10 to 13).

The composition of the molding materials and of the comparative molding materials are shown in Table 1.

TABLE 1

| Example | Phosphine chelate ligand | Preparation according to | Potassium iodide | Polyamide (% by weight) Glass fiber content) (GF) (% by weight) |
|---|---|---|---|---|
| 1 | Bis(diphenylphosphino)methane | b) | + | PA66 100%/— |
| 2 | 1,2-Bis(diphenylphosphino)ethane | b) | − | PA6 70%/GF 30% |
| 3 | 1,2-Bis(diphenylphosphino)ethane | a) | + | PA66 100%/— |
| 4 | 1,2-Bis(diphenylphosphino)ethane | b) | + | PA66 70%/GF 30% |
| 5 | 1,2-Bis(diphenylphosphino)ethane | a) | − | PA66 70%/GF 30% |
| 6 | 1,3-Bis(diphenylphosphino)propane | a) | + | PA66 70%/GF 30% |
| 7 | 2,2'-Bis(diphenylphosphino)-1,1'-binaphthyl | a) | + | PA66 70%/GF 30% |
| 8 | 1,3-Bis(dicyclohexylphosphino)propane | a) | + | PA66 70%/GF 30% |
| 9 | 1,3-Bis[(2-mercaptoethyl)cyclohexylphosphino]propane | a) | + | PA66 70%/GF 30% |
| 10 | Triphenylphosphine | b) | + | PA66 100%/— |
| 11 | Triphenylphosphine | a) | + | PA66 100%/— |
| 12 | Triphenylphosphine | b) | − | PA66 70%/GF 30% |
| 13 | Triphenylphosphine | b) | + | PA6 70%/GF 30% |

C. Performance Characteristics of the Thermoplastic Molding Materials of Examples 1 to 13

The decrease in the impact strength values and in the tensile modulus of elasticity after storage at elevated temperatures is a measure of the stabilizing effect of additives. For this purpose, both values were determined in each case before and after storage for 240 and 600 hours, respectively, at 150° C. in a through-circulation oven.

The sample preparation and the measurement of the Charpy impact strength (impact bending test) were carried out according to DIN 53453.

The sample preparation and the measurement of the tensile modulus of elasticity (tensile test) were carried out according to DIN 53455.

TABLE 2

| | Charpy impact strength Charpy [kJ/m$^2$] | | | Tensile modulus of elasticity [MPa] | | |
|---|---|---|---|---|---|---|
| Example | after 0 h | after 240 h | after 600 h | after 0 hr | after 240 h | after 600 h |
| 1 | n.d. | 45 | 38 | 3050 | 2850 | 2600 |
| 2 | 78 | 58 | 56 | 9650 | 9950 | 9700 |
| 3 | n.d. | 48 | 42 | 3100 | 3000 | 2750 |
| 4 | 81 | 69 | 58 | 9600 | 9800 | 9600 |
| 5 | 80 | 61 | 49 | 9650 | 10,050 | 9550 |
| 6 | 80 | 67 | 54 | 9550 | 10,000 | 9650 |
| 7 | 81 | 64 | 50 | 9600 | 9950 | 9650 |
| 8 | 80 | 65 | 49 | 9650 | 10,100 | 9750 |
| 9 | 81 | 68 | 58 | 9550 | 9700 | 9600 |
| 10 | n.d. | 12 | 5 | 3050 | 2600 | <1500 |
| 11 | n.d. | 13 | 4 | 2960 | 2550 | <1500 |
| 12 | 77 | 28 | 25 | 9600 | 11,500 | 9000 |
| 13 | 79 | 30 | 27 | 9650 | 11,200 | 8850 | n.d. = not determined

All products 1–9 of the novel composition show improved heat distortion resistance in combination with improved hue after compounding.

D. Preparation of the Phosphine Chelate Ligand from Example 9 a. Preparation of Cyclohexylphosphonyl Dichloride

An oxygen stream was passed into a mixture of 337 g (4 mol) of cyclohexane and 275 g (2 mol) of phosphorus trichloride while stirring and cooling so that the internal temperature remained in a range from 15 to 25° C.

The reaction mixture was subjected to fractional distillation under reduced pressure. 115 g of cyclohexylphosphonyl dichloride (boiling point 141° C. at 1.2 mmHg) were obtained as an oil, which crystallized as white needles.

b. Preparation of Cyclohexyl Monophosphine

A solution of 60 g (0.3 mol) of cyclohexylphosphonyl dichloride in 100 ml of ether was added dropwise, under a nitrogen atmosphere, to a cooled mixture of 22 g (0.58 mol) of lithium aluminum hydride in 400 ml of ether at a rate sufficiently slow that the temperature did not exceed 15° C.

Refluxing was then carried out for a further 30 minutes, the mixture was cooled and 500 ml of semiconcentrated hydrochloride were added. The organic phase was separated off, dried over magnesium sulfate and subjected to fractional distillation (boiling point 143–146° C.). Yield: 17 g c. Preparation of 1,3-bis(cyclohexylphosphino)propane

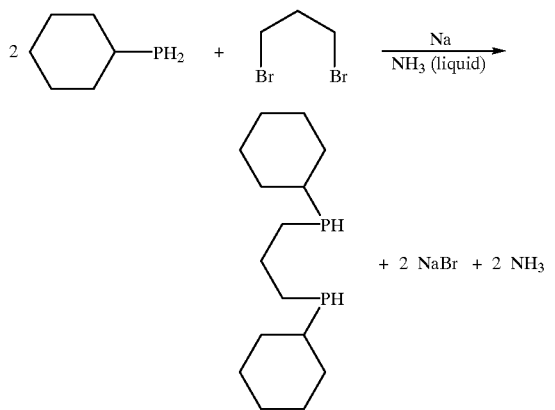

2 g (0.086 mol) of sodium were dissolved in 215 ml of liquid ammonia and a pinch of rust was added. After 4 hours, all the sodium had been converted into the amide. 10 g (0.086 mol) of cyclohexylmonophosphine were metered into this suspension at −60° C. and stirring was carried out at this temperature for 10 hours. 8.68 g (0.043 mol) of 1,3-dibromopropane, dissolved in 10 ml of ether, were added dropwise to the resulting greenish-yellow solution in the course of 90 minutes. After a further 30 minutes, the cooling was removed and the evaporating ammonia was replaced by ether. The ether mixture was refluxed for 30 minutes. The mixture was worked up by adding 250 ml of ether and 200 ml of water and carrying out extraction. The organic phase was dried over sodium sulfate and evaporated down and the residue was distilled under reduced pressure.

d. Preparation of 1,3-bis[(2-mercaptoethyl)cyclohexylphosphino]propane

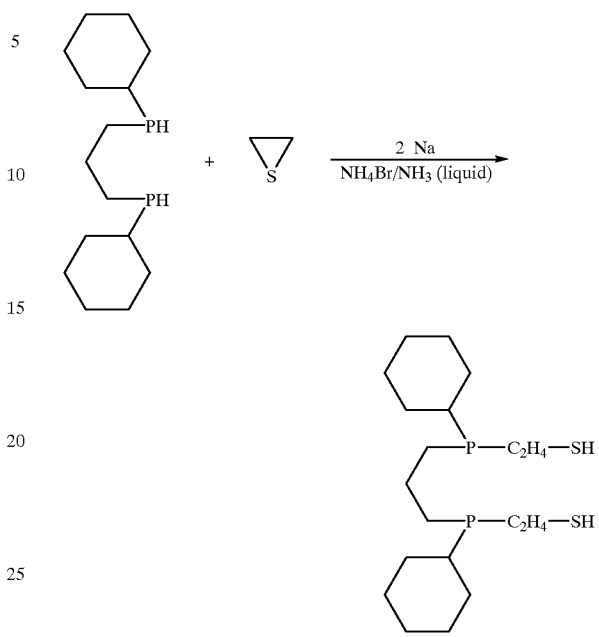

4.6 g (0.2 mol) of sodium were dissolved in 100 ml of liquid ammonia, and 27.2 g (0.1 mol) of 1,3-bis(cyclohexylphosphino)propane were metered in at −50° C. The mixture was stirred for 4 hours at this temperature, and 12 g (0.2 mol) of thiirane were then metered in. After evaporation of the ammonia, stirring was carried out for 2 hours at 40° C. The reaction mixture was worked up by distillation.

We claim:

1. A thermoplastic molding material containing from 30 to 100% by weight of a mixture of polyamide and a stabilizing amount of a copper compound obtained by reacting copper (I) salts with a phosphine chelate ligand of the formula I or II

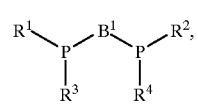

where $B^1$ is $C_1$–$C_6$-alkylene, naphthylene, phenylene or benzylene, $R^1$ and $R^2$, independently of one another, are each $C_1$–$C_8$-alkyl, $C_5$–$C_8$-cycloalkyl or phenyl which is unsubstituted or monosubstituted to pentasubstituted by $C_1$–$C_4$-alkyl, $R^3$ and $R^4$, independently of one another, are each $C_1$–$C_8$-alkyl, $C_5$–$C_8$-cycloalkyl, phenyl which is unsubstituted or substituted by $C_1$–$C_4$-alkyl, or are each —$B^1$—$PR^2R^2$, $B^2$—$SR^5$ or $B^2$—$OR^5$, and $R^3$ and $R^4$ together are —$B^2$—$PR^2$—$B^3$— or —$B^2$—$PR^2$—$B^3$—$PR^2$—$B^4$—, and $B^2$, $B^3$ and $B^4$, independently of one another, are each $C_1$–$C_6$-alkylene, naphthylene, phenylene or benzylene and

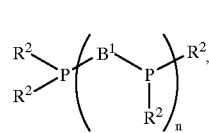
(II)

where
- $B_1$ is $C_1$–$C_6$-alkylene, naphthylene, phenylene or benzylene,
- $R^2$ is $C_1$–$C_8$-alkyl, $C_5$–$C_8$-cycloalkyl or phenyl which is unsubstituted or monosubstituted to pentasubstituted by $C_1$–$C_4$-alkyl and
- n is 1, 2 or 3 and from 0 to 70% by weight of further additives.

2. A thermoplastic molding material as claimed in claim 1, wherein the copper compound is present in an amount of from 10 to 1000 ppm, calculated as copper and based on polyamide.

3. A thermoplastic molding material as claimed in claim 1, which contains up to 70% by weight of further additives.

4. A thermoplastic molding material as claimed in claim 1, in which the copper compound is obtained by reacting a copper halide with a phosphine chelate ligand.

5. A thermoplastic molding material as claimed in claim 1, in which the copper(I) compound is obtained by reacting a copper(I) salt with a phosphorus-sulfur compound of the formula (III)

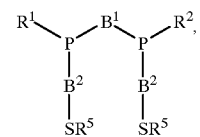
(III)

where
- $B^1$ and $B^2$, independently of one another, are each $C_1$–$C_6$-alkylene, naphthylene, phenylene or benzylene,
- $R^1$ and $R^2$, independently of one another, are each $C_1$–$C_8$-alkyl, $C_5$–$C_8$-cycloalkyl or phenyl which is unsubstituted or substituted by $C_1$–$C_4$-alkyl and
- $R^5$ is $C_1$–$C_4$-alkyl or hydrogen.

6. A thermoplastic molding material as claimed in claim 1, which furthermore contains from 1 to 3000 ppm, based on polyamide, of an alkali metal halide.

7. A method of using a thermoplastic molding material as claimed in claim 1 for the production of fibers, films and moldings.

8. A fiber, film or molding obtained from a thermoplastic molding material as claimed in claim 1.

* * * * *

UNITED STATES PATENT AND TRADEMARK OFFICE
CERTIFICATE OF CORRECTION

PATENT NO.: 6,011,099

DATED: January 4, 2000

INVENTOR(S): GRUTKE et al.

It is certified that error appears in the above-identified patent and that said Letters Patent is hereby corrected as shown below:

Col. 14, claim 1, line 42, "lipand" should be --ligand--.

Col. 16, claim 7, line 22, "of using" should be --to make--.

Col. 16, claim 7, line 24, after "moldings" insert --comprises the steps of compounding a copper compound and a polyamide, extruding the resulting mixture, and drying the resulting granules."

Signed and Sealed this

Nineteenth Day of September, 2000

Q. TODD DICKINSON

Attest:

Attesting Officer

Director of Patents and Trademarks